United States Patent
Radovic

(10) Patent No.: US 10,561,715 B2
(45) Date of Patent: Feb. 18, 2020

(54) PLANTAR HEEL PAIN SYNDROME TREATMENT

(71) Applicant: Philip Andrew Radovic, San Clemente, CA (US)

(72) Inventor: Philip Andrew Radovic, San Clemente, CA (US)

(*) Notice: Subject to any disclaimer, the term of this patent is extended or adjusted under 35 U.S.C. 154(b) by 0 days.

(21) Appl. No.: 16/202,008

(22) Filed: Nov. 27, 2018

(65) Prior Publication Data

US 2019/0262439 A1 Aug. 29, 2019

Related U.S. Application Data

(60) Provisional application No. 62/635,454, filed on Feb. 26, 2018.

(51) Int. Cl.
| | | |
|---|---|---|
| *A61K 38/48* | (2006.01) | |
| *A61H 39/08* | (2006.01) | |
| *A61M 5/32* | (2006.01) | |
| *A61P 25/02* | (2006.01) | |
| *A61K 9/00* | (2006.01) | |

(52) U.S. Cl.
CPC ......... *A61K 38/4893* (2013.01); *A61H 39/08* (2013.01); *A61K 9/0019* (2013.01); *A61M 5/32* (2013.01); *A61P 25/02* (2018.01); *A61H 2201/105* (2013.01); *A61H 2205/125* (2013.01); *A61M 2205/05* (2013.01); *A61M 2210/086* (2013.01)

(58) Field of Classification Search
CPC .......................... A61K 38/4893; A61K 9/0019
See application file for complete search history.

(56) References Cited

U.S. PATENT DOCUMENTS

| | | | | |
|---|---|---|---|---|
| 9,211,248 | B2 | 12/2015 | Dake | |
| 2003/0224019 | A1* | 12/2003 | O'Brien | A61K 38/4893 424/239.1 |
| 2010/0331883 | A1* | 12/2010 | Schmitz | A61B 10/0275 606/249 |
| 2012/0143056 | A1* | 6/2012 | Slayton | A61N 7/02 600/439 |
| 2013/0202636 | A1* | 8/2013 | Dake | A61K 9/0014 424/192.1 |
| 2014/0343542 | A1* | 11/2014 | Karnik | A61B 18/02 606/24 |
| 2018/0333472 | A1* | 11/2018 | Koman | A61K 38/4893 |

OTHER PUBLICATIONS

Muscles of the foot (Year: 2017).*
The Use of Dry Needling and Myofascial Meridians in a case of Plantar Fasciitis by Akhbari et al. (Journal of Chiropractic Medicine) (Year: 2014).*
STIC search result 1 (Year: 2019).*
STIC search result 2 (Year: 2019).*
STIC search result 3 (Year: 2019).*
Iborra-Marcos et al. ("*Intratissue Percutaneous Electrolysis vs Corticosteroid Infiltration for the Treatment of Plantar Fasciosis*") (Year: 1997).*
O'Brien ("Injection Techniques for Botulinum Toxin using Electromyography and Electrical Stimulation") (Year: 2018).*
O'Brien ("Injection Techniques for Botulinum Toxin using Electromyography and Electrical Stimulation") Examiner notes: this document shows the published date of the article which is Feb. 13, 2018 (Year: 2018).*
DaxibotulinumtoxinA for Injection for the Treatment of Plantar Fasciitis; Available on the World Wide Web at https://clinicaltrials.gov/ct2/show/NCT03825315?id=NCT03825315&rank=1&load=cart; Jan. 31, 2019.
Ahmad, J., et al., Treatment of Plantar Fasciitis With Botulinum Toxin: A Randomized, Controlled Study, Foot & Ankle International, vol. 38, No. 1, pp. 1-7, 2017.
Babcock, M.S., et al., Treatment of Pain Attributed to Plantar Fasciitis with Botulinum Toxin A: A Short-Term, Randomized, Placebo-Controlled, Double-Blind Study, American Journal of Physical Medicine & Rehabilitation, vol. 84, No. 9, pp. 649-654.
Barrett, S.L., A Guide to Neurogenic Etiologies of Heel Pain, PodiatryToday, vol. 18, No. 11, pp. 36-44, 2005.
Benjamin, M., et al., The fascia of the limbs and back—a review, Journal of Anatomy, vol. 214, pp. 1-18, 2009.
Borodic, G. et al., Botulinum Toxin Therapy for Pain and Inflammatory Disorders: Mechanisms and Therapeutic Effects, Expert Opinion on Investigational Drugs, vol. 10, No. 8, pp. 1531-1544, 2001.
Buchbinder, R., Plantar Fasciitis, The New England Journal of Medicine, vol. 350, pp. 2159-2166, 2004.
Chen, J.T-N., et al., Effective Conservative Treatment for Managing Painful Hallux Valgus, Medical Research Archives, vol. 4, No. 5, pp. 1-9, 2016.
Cheshire, W.P., et al., Botulinum toxin in the treatment of myofascial pain syndrome, International Association for the Study of Pain, vol. 59, No. 1, pp. 65-69, 1994.
Cheung, J.T-K., et al., Consequences of Partial and Total Plantar Fascia Release: A Finite Element Study, Foot & Ankle International, vol. 27, No. 2, pp. 125-132, 2006.
Coughlin, M.J., Chapter 12, Plantar Heel Pain, Surgery of the Foot and Ankle, 8th Ed., vol. 1, Edited by Lee, T.h., Maurus, P.B., pp. 695-698, Mosby, 2007.
Coughlin, M.J., Chapter 11, Diseases of the Nerves, Surgery of the Foot and Ankle, 8th Ed., vol. 1, Edited by Lew C. Schon, Roger Mann, pp. 663-670, Mosby, 2007.

(Continued)

*Primary Examiner* — Nathan R Price
*Assistant Examiner* — Dung T Ulsh
(74) *Attorney, Agent, or Firm* — Knobbe, Martens, Olson & Bear, LLP

(57) ABSTRACT

Plantar Heel Pain Syndrome can be of one or more etiologies and symptoms which refutes the mistaken tendency to categorize all plantar heel pain singularly as either plantar fasciitis or fasciosis. Recognizing that there is likely an interplay of inflammatory, degenerative and neuropathic etiologic conditions of this often-difficult malady to treat, a novel injection paradigm of botulinum toxin is explored in the treatment of 4 distinct presentations of Plantar Heel Pain Syndrome with promising results.

10 Claims, No Drawings

(56) References Cited

OTHER PUBLICATIONS

Cui, M., et al., Subcutaneous administration of botulinum toxin a reduces formalin-induced pain, Pain, vol. 107, pp. 125-133, 2004.
Deheer, P., A Closer Look at Heel Pain and Baxter's Neuritis, pp. 1-5, 2013.
Dia, R.C.R., et al., Botulinum Toxin for the Treatment of Chronic Pain. Review of the Evidence, Colombian Journal of Anesthesiology, vol. 42, No. 3, pp. 205-213, 2014.
Diaz-Llopis, I.V., et al., Botulinum Toxin Type A in Chronic Plantar Fasciitis: Clinical Effects One Year After Injection, Clinical Rehabilitation, vol. 27, No. 8, pp. 681-685, 2013.
Diaz-Llopis, I.V., et al., Randomized Controlled Study of the Efficacy of the Injection of Botulinum Toxin Type A Versus Corticosteroids in Chronic Plantar Fasciitis: Results at One and Six Months, Clinical Rehabilitation, vol. 26, No. 7, pp. 594-606, 2011.
Donovan, A., et al., MR Imaging of Entrapment Neuropathies of the Lower Extremity Part 2. The Knee, Leg, Ankle, and Foot, RadioGraphics, vol. 30, pp. 1001-1019, 2010.
Foster, L. et al., Botulinum Toxin A and Chronic Low Back Pain: A Randomized, Double-Blind Study, Neurology, vol. 56, No. 10, pp. 1290-1293, 2001.
Hendrix, C.L., et al., Entrapment Neuropathy: The Etiology of Intractable Chronic Heel Pain Syndrome, The Journal of Foot and Ankle Surgery, vol. 37, No. 4. pp. 273-279, 1998.
Huang, Y-C., et al., Ultrasonographic Guided Botulinum Toxin Type A for Plantar Fasciitis: An Outcome-Based Investigation for Treating Pain and Gait Changes, Journal of Rehabilitation Medicine, vol. 42, No. 2, pp. 136-140, 2010.
Jarvis, S. et al., Pilot Study of Botulinum Toxin Type A in the Treatment of Chronic Pelvic Pain Associated With Spasm of the Levator Ani Muscles, Australian and New Zealand Journal of Obstetrics and Gynaecology, vol. 44, No. 1, pp. 46-50, 2004.
Lemont, H., et al., Plantar Fasciitis: A Degenerative Process (Fasciosis) Without Inflammation, Journal of the American Podiatric Medical Association, vol. 93, No. 3, pp. 234-237, 2003.
Mahowald, S., et al., The Correlation Between Plantar Fascia Thickness and Symptoms of Plantar Fasciitis, Journal of the American Podiatric Medical Association, vol. 101, No. 5, pp. 385-389, 2011.
Maida, E., et al., Sonographically Guided Deep Plantar Fascia Injections, Journal of Ultrasound in Medicine, vol. 32, No. pp. 1451-1459, 2013.
Mardani-Kivi, M., et al., Treatment Outcomes of Corticosteroid Injection and Extracorporeal Shock Wave Therapy as Two Primary Therapeutic Methods for Acute Plantar Fasciitis: A Prospective Randomized Clinical Trial, The Journal of Foot and Ankle Surgery, vol. 54, pp. 1047-1052, 2015.
Martin, R.L., et al., Evidence of Validity for the Foot and Ankle Ability Measure (FAAM), Foot & Ankle International, vol. 26, No. 11, pp. 968-983, 2005.
Melero-Suarez, R., et al., Evaluation of the Analgesic Effect of Combination Therapy on Chronic Plantar Pain Through the Myofascial Trigger Points Approach, Journal of the American Podiatric Medical Association, vol. 108, No. 1, pp. 27-32, 2018.
Mustafa, G., et al., Anti-Nociceptive Effect of a Conjugate of Substance P and Light Chain of Botulinum Neurotoxin Type A, Pain, vol. 154, No. 11, pp. 2547-2553, 2013.
Myerson, M.S., Chapter 34, Plantar Heel Pain, Foot and Ankle Disorders, vol. 2, Edited by Pfeffer, G.B., p. 838, WB Saunders, Philadelphia, 2000.
Peterlein, C. et al., Is Botulinum Toxin A Effective for the Treatment of Plantar Fasciitis?, The Clinical Journal of Pain, vol. 28, No. 6, pp. 527-533, 2012.
Placzek, R., et al., Treatment of Chronic Plantar Fasciitis With Botulinum Toxin A, Preliminary Clinical Results, Clinical Journal of Pain, vol. 22, No. 2, pp. 190-192, 2006.
Placzek, R., et al., Treatment of Chronic Plantar Fasciitis With Botulinum Toxin A: An Open Case Series With a 1 Year Follow Up, Annals of the Rheumatic Diseases, vol. 64, pp. 1659-1661, 2005.
Pribut, S.M., Current Approaches to the Management of Plantar Heel Pain Syndrome, Including the Role of Injectable Corticosteroids, Journal of the American Podiatric Medical Association, vol. 97, No. 1, pp. 68-74, 2007.
Radovic, P., et al., Nonsurgical Treatment for Hallux Abducto Valgus with Botulinum Toxin A, Journal of the American Podiatric Medical Association, vol. 98, No. 1, pp. 61-65, 2008.
Radovic, P., Treatment of "Plantar Fasciitis"/Plantar Heel Pain Syndrome with Botulinum Toxin-A Novel Injection Paradigm, Nov. 27, 2018.
Rahbar, M., et al., A Comparison of the Efficacy of Dry-Needling and Extracorporeal Shockwave Therapy for Plantar Fasciitis: A Randomized Clinical Trial, Iranian Red Crescent Medical Journal, vol. 20, No. 9, e68908, 2018.
Riddle, D.L., et al., Risk Factors for Plantar Fasciitis: A Matched Case-Control Study, The Journal of Bone and Joint Surgery, vol. 85-A, No. 5, pp. 872-877, 2003.
Sammarco, G. et al., Surgical Treatment of Recalcitrant Plantar Fasciitis, Foot & Ankle International, vol. 17, No. 9, pp. 520-526, 1996.
Schneider, H.P., et al., American College of Foot and Ankle Surgeons Clinical Consensus Statement: Diagnosis and Treatment of Adult Acquired Infracalcaneal Heel Pain, The Journal of Foot and Ankle Surgery, vol. 57, pp. 370-381, 2018.
Silberstein, S. et al., Botulinum toxin type A as a migraine preventive treatment, Headache, vol. 40, pp. 445-450, 2000.
Singh, J., Use of Botulinum Toxin in Musculoskeletal Pain, F1000Research, vol. 2, No. 52, pp. 1-22, 2013.
Soysa, A., et al., Importance and Challenges of Measuring Intrinsic Foot Muscle Strength, Journal of Foot and Ankle Research, vol. 5, No. 29, pp. 1-14, 2012.
Spasticity in adults: management using botulinum toxin, National Guidelines, The Royal College of Physicians, 124 pages, 2018.
Stecco, C., et al., Plantar Fascia Anatomy and Its Relationship With Achilles Tendon and Paratenon, Journal of Anatomy, vol. 223, pp. 665-676, 2013.
Suputtitada, A., Local Botulinum Toxin Type A Injections in the Treatment of Spastic Toes, American Journal of Physical Medicine & Rehabilitation, vol. 81, No. 10, pp. 770-775, 2002.
Tahririan, M.A., et al., Plantar fasciitis, Journal of Research in Medical Sciences, vol. 17, pp. 799-804, 2012.
Uğurlar, M., et al., Effectiveness of Four Different Treatment Modalities in the Treatment of Chronic Plantar Fasciitis During a 36-Month Follow-Up Period: A Randomized Controlled Trial, The Journal of Foot & Ankle Surgery, vol. 57, No. 5, pp. 913-918, 2018.
Wheeler, A. et al., A Randomized, Double-Blind, Prospective Pilot Study of Botulinum Toxin Injection for Refractory, Unilateral, Cervicothoracic, Paraspinal, Myofascial Pain Syndrome, Spine, vol. 23, No. 15, pp. 1662-1666, 1998.
Willis, B., et al., Pain Scale for Plantar Fasciitis, The Foot and Ankle Online Journal, vol. 2, No. 5, pp. 1-6, 2009.
Wu, K.P-H., et al., Botulinum Toxic Type A Injections for Patients With Painful Hallux Valgus: A Double-Blind. Randomized Controlled Study, Clinical Neurology and Neurosurgery, vol. 129 S1, pp. S58-S62, 2015.
Zelen, C.M., et al., Prospective, Randomized, Blinded, Comparative Study of Injectable Micronized Dehydrated Amniotic/Chorionic Membrane Allograft for Plantar Fasciitis—A Feasibility Study, Foot & Ankle International, vol. 34, No. 10, pp. 1332-1339, 2013.
Zhang, T., et al., The efficacy of botulinum toxin type A in managing chronic musculoskeletal pain: a systematic review and meta analysis, Inflammopharmacology, vol. 19, pp. 21-34, 2011.
U.S. Appl. No. 62/507,628 (Application of US 2018/0333472 A1), filed May 17, 2017, Koman.
Chou, L-W., et al., Serial ultrasonographic findings of plantar fasciitis after treatment with botulinum toxin A: a case study, Archives of Physical Medicine and Rehabilitation, vol. 92, No. 2, pp. 316-319, 2011.
International Search Report & Written Opinion, dated May 10, 2019, in International Patent Application No. PCT/US2019/019302.
Thiagarajah, A.G., How effective is acupuncture for reducing pain due to plantar fasciitis? Singapore Medical Journal, vol. 58, No. 2, pp. 92-97, 2017.

(56) References Cited

OTHER PUBLICATIONS

Del Toro, D.R., et al., Abductor Hallucis False Motor Points: Electrophysiologic Mapping and Cadveric Dissection, Muscle and Nerve, vol. 19, pp. 1138-1143, 1996.

Matak, I., et al., Mechanisms of Botulinum Toxin Type A Action on Pain, Toxins, 11, 459, 2019, doi:10.3390/toxins11080459, 26 pages.

Narita, H., et al., Does the Location of the Motor Point Identified with Electrical Stimulation Correspond to that Identified with the Gross Anatomical Method?, J. Phys. Ther. Sci., vol. 23, pp. 737-739, 2011.

* cited by examiner

PLANTAR HEEL PAIN SYNDROME TREATMENT

PRIORITY AND CROSS-REFERENCE TO RELATED APPLICATIONS

This application claims the benefit of U.S. Provisional Application No. 62/635,454, filed Feb. 26, 2018, and entitled BOTULINUM TOXIN TREATMENT FOR PLANTAR FASCIITIS, which is hereby incorporated by reference in its entirety.

BACKGROUND

Field

The present disclosure is generally related to treatment of Plantar Heel Pain Syndrome. Some embodiments of the present disclosure are related to treatment of Plantar Heel Pain Syndrome with Botulinum Toxin.

Description of the Related Art

Plantar Heel Pain Syndrome can be of one or more etiologies and symptoms which refutes the mistaken tendency to categorize all plantar heel pain singularly as either plantar fasciitis or fasciosis.

Some prior art treatments of Plantar Heel Pain Syndrome have been based on an attribution of the mechanism of action to paralysis of certain intrinsic muscles, but proposed injecting neurotoxin into the fascia itself. Certain prior art publications provide only a general description of a particular singular injection. Typically, such injection is into the insertion area of the plantar fascia or the "area of pain". For example, Placzek et al., reported in "Treatment of Chronic Plantar Fasciitis With Botulinum Toxin A—Preliminary Clinical Results" that "The injection was administered in a fan-shaped manner directly at the calcaneal origin of the plantar fascia".

In another paper, Babcock et al., "A one, 4 direction subfascial injection at the painful area of the plantar fascial insertion" was applied. This paper mentions both Abductor halluces and Quadratus Plantae paralysis as a mechanism for Plantar Heel Pain Sydrome, but not specifically as an injection protocol. Rather, a four-direction subfascial injection was applied. Reference is made somewhat unclearly to both Adductor and Abductor halluces muscles. Still another paper reports on injection into the flexor digitorum brevis (FDB) using electromyographic (EMG) monitoring to confirm targeting at the FDB.

However, none of the prior techniques have been fully effective at providing long-term and repeatable relief for Plantar Heel Pain Syndrome. Thus, a need remains for such an effective protocol.

SUMMARY

A method of treating Plantar Heel Pain Syndrome/Plantar Fasciitis in a patient in need thereof, includes injecting botulinum toxin into the insertional plantar fascia area of each of the Abductor Hallucis and Quadratus Plantae muscles in a foot of the patient affected by the Plantar Heel Pain Syndrome. The toxin can be at the intrinsic foot muscle origins of each of the Abductor Hallucis and Quadratus Plantae muscles at the plantar medial calcaneus.

In one embodiment, the toxin can be injected using a needle. Placement of the needle at the insertional plantar fascial area of each of the Abductor Hallucis and Quadratus Plantae muscles can be confirmed by muscle/nerve stimulation.

In one embodiment, the toxin is first injected into the Abductor Hallucis, and in another embodiment, the toxin is injected into both the Abductor Hallucis and Quadratus Plantae in the same procedure. For example, the toxin can be injected into the Quadratus Plantae more than one hour after toxin is injection into the Abductor Hallucis.

In certain other embodiments, the method can also include one or more of injecting botulinum toxin into the plantar fascia, injecting a dry needle into the plantar fascia, or applying botulinum toxin topically to the skin in the area of pain caused by the Plantar Heel Pain Syndrome/Plantar Fasciitis.

DETAILED DESCRIPTION

Some embodiments of the present disclosure are related to treatment of Plantar Heel Pain Syndrome (also known as "Plantar Fasciitis") with Botulinum Toxin based on a novel injection paradigm. Some embodiments of the present disclosure are related to treatment of Plantar Heel Pain Syndrome (also known as "Plantar Fasciitis") with Botulinum Toxin. Some embodiments of the present disclosure are related to treatment of Plantar Heel Pain Syndrome (also known as "Plantar Fasciitis") with Botulinum Toxin based on a particular injection paradigm.

Plantar Heel Pain Syndrome can be of one or more etiologies and symptoms which refutes the mistaken tendency to categorize all plantar heel pain singularly as either plantar fasciitis or fasciosis. Plantar Fasciitis is the inflammation/micro tearing of a ligament, the plantar fascia. It is often mistakenly attributed to other associated heel pain "syndromes" which may even be more prevalent such as Baxter's neuritis, Tarsal Tunnel Syndrome, Heel spur Syndrome, and/or Plantar fasciosis. Recognizing that there is likely an interplay of inflammatory, degenerative and neuropathic etiologic conditions of this often-difficult malady to treat, a novel injection paradigm of botulinum toxin is explored in the treatment of 4 distinct presentations of Plantar Heel Pain Syndrome with promising results.

Terminology for most plantar heel pain has been inconsistently described in the literature and is typically and erroneously defaulted to "Plantar Fasciitis". This reflects its multifactorial, poorly understood and often disputed etiology 1,2,3,4. Barrett et al have stated: "the presence of multiple etiology refutes the mistaken tendency to categorize all heel pain as plantar fasciitis when the correct terminology is plantar fasciosis". However, he also describes the frequent interplay between the presence of plantar fasciopathy and nerve entrapment 5. Therefore, the term Plantar Heel Pain Syndrome to describe the condition is preferred. It can be attributed to one or a combination inflammatory, degenerative and neuropathic conditions localized at the plantar heel 4,5,6. Common associated inflammatory processes are plantar fasciitis from acute micro tears of the fascia, insertional periostitis, neuritis and myositis 7,8,9. Degenerative processes of painful fasciosis are attributed to chronic repetitive micro injury and scaring with resultant avascularity 10. Neuropathic conditions such as Baxter's Neuritis (inferior calcaneal nerve entrapment), tarsal tunnel syndrome, medial plantar nerve entrapment, lateral plantar nerve entrapment and medial calcaneal nerve entrapment can be due to compression/entrapment or sensitization from either an inflammatory or avascular plantar heel condition 9. To be clear, Plantar Heel Pain Syndrome does not include many other causes of heel pain such as plantar fascia rupture, Calcaneal fractures, bone cyst, soft tissue masses/bursae, tendon pathology, gout, arthritis, fat pad atrophy, calcaneal bone spur, calcifications and various dermal conditions that that my cause heel pain which are typically referenced in the catch all "plantar calcaneal heel pain".

The plantar fascia is also well innervated, with both free and encapsulated nerve endings, such as Pacini and Ruffini corpuscles. These nerve endings are particularly abundant where the plantar fascia joins with the fasciae of the abductor hallucis and abductor digiti minimi muscles and where the flexor muscles insert [(quadratus plantar)].

Again, although frequently attributed to plantar fasciitis, plantar heel pain affects about 1 in 10 persons at some point in their life, and nearly 2 million people seek treatment for it annually 11. Plantar medial heel pain attributed to plantar fasciitis is the most common condition podiatrists see in most practices and it is commonly claimed that over 90 percent of patients are cured with conservative treatment 12. However, this is typically attributed to a shotgun treatment approach or progressive and protracted escalation of intervention of non-operative treatments consisting of plantar fascia and gastrocnemius-soleus stretching, icing, NSAID's, heel cups, OTC shoe inserts, custom functional foot orthoses, corticosteroid injection, night splints, change in shoe gear, physical therapy and immobilization casts 1,4,13. These treatments can protract over many months/years culminating in significant cost not to mention that of diagnostic testing that can include MRI, CT, EMG, YS, PSSD and bone scans. Yet if any one or more of these treatments are successful, can one really assume it was plantar fasciitis? And if not, is it then plantar fasciosis or a neuropathic condition, or inter-related combination of conditions? In recent years we have seen an expanded causation for "plantar fasciitis" along with a multitude of various treatments that target these etiologies. Along with the above "tried and true" conservative treatments, some employ; neuropathic pain agents (gabapentin), PRP, EPAT/ESWT, prolotherapy, dry-needling, laser and amniotic/chorionic membrane allograft injection 13,14,15,16.

Upon failure of conservative management or "non-surgical" procedures, various operative procedures can be offered which include coblation, radiofrequency debridement, decompression and release16. However, with surgical intervention there are risks which include infection, delayed healing, and nerve injury or entrapment. Long term complications may be due to postoperative sequelae, which can include medial or lateral column collapse and pain, and recurrence of heel pain 18.

Botulinum toxin is a protein produced by the anaerobic bacterium *Clostridium botulinum*. Seven serotypes (A-G) of botulinum neurotoxin exist as well as recombinant species. Type A was the first to be FDA approved and is most frequently used 19,20. In small amounts botulinum toxin A (BTX A) causes muscle paralysis by blocking presynaptic release of neurotransmitter acetylcholine. Acetylcholine plays a vital role in sending signals from the nerve to the muscle causing movement. BTX A blocks the synaptic transmission and causes the muscle to which the nerve is attached to become paralyzed.

The clinical applications for BTX A have been expanding since its first use in the 1980's for strabismus, misalignment of the eyes. The scope of treatment in the lower extremity has broadened, suggesting its use not only for spastic foot or ankle seen in cerebral palsy patients but also for spastic toes 22, plantar hyperhidrosis 23, hallux abducto valgus23-26, and plantar fasciitis 27-31.

BTX A has also proven to have analgesic and anti-inflammatory properties31-38. In recent years, BTX A has been used for treating chronic muscular and neuropathic pain, such as migraine, myofascial pain syndrome and *piriformis* syndrome (38-42). BTX A has been found to have anti-nociceptive and anti-allodynia effects and acts by modulating pain neurotransmitters including sub-stance P, glutamate and anti-inflammatory reactions (33).

Several studies have shown success in treatment of "plantar fasciitis" with BTX A injection. Most are non-specific in their injection target(s) other than the area of the plantar fascia calcaneal origin, plantar medial heel, area of pain, or in combination with the Flexor Hallucis *brevis* muscle 27-31, 43-45. Additionally, the subject inclusion diagnosis of the "plantar fasciitis" in these studies may be a catch-all term of a syndrome consisting of one or a combination of several conditions that contribute to Plantar Heel Pain Syndrome. This may possibly explain some variations in treatment efficacy.

Without being limited by any particular theory, the case reports in this disclosure explore the idea that Plantar Heel Pain Syndrome being a neuropathic condition whether of mechanical, inflammatory or degenerative etiology can be successfully treated with a very specific botulinum injection paradigm targeting the Abductor Hallucis and Quadratus Plantae (insertional plantar fascia area) intrinsic foot muscle origins at the plantar medial calcaneus regardless of the specific Plantar Heel Pain Syndrome etiology or combination thereof.

Given the high degree of variability of the neuroanatomy of the medial aspect of the heel, the unreliability of EMG, limitations of PSSD, MRI, Tinel's sign or Valleix's Point, it can be difficult and imprecise to isolate and determine which nerve/branch is involved. An exception maybe the medial calcaneal branch which is sensory, superficial and end branch making it relatively easy to isolate with nerve block. However, there is a consistent anatomic approximation of these medial heel nerves to the Abductor Hallucis and/or Quadratus Plantae 46-48. Surgical decompression of the fascia between these two muscles has been a well-documented treatment for recalcitrant heel pain attributed to Baxter's neuritis, Tarsal Tunnel Syndrome and "plantar fasciitis"6, 48. And although a superficial nerve, the medial calcaneal nerve has a consistent anatomical approximation the origin of the Abductor Hallucis. Also of particular interest is the high density of nerve ganglia associated with the origin of the intrinsic flexors; Quadratus Plantae muscle at the calcaneus 49,50. It thus seems logical that paralyzing these two muscles with precise BTX A injection under electronic stimulation will decompress to some extent any one or all of these nerves relieving the neuropathic component of Plantar Heel Pain Syndrome and synergizing the analgesic and anti-inflammatory effects of the toxin. This method is more precise than that of "blind" or even ultrasonic guided injection due to the insertional and approximate variability of the intrinsic muscles with the plantar fascia 51. Also, isolation via EMG of theses intrinsic muscles can be very difficult, particularly between Flexor Hallucis *Brevis*, Flexor Digitorum *Brevis* and Quadratus Plantae.

The inventor has discovered that a large part of these "Heel Pain Syndromes" are attributable to a neuropathic condition, primarily due to the over activity, hypertrophy or spasticity of 2 intrinsic muscles which cause a compression to the medial and lateral plantar nerves and variable associated branches; Abductor Hallucis and Quadratus Plantae. Accordingly, in an embodiment of the present disclosure, a method is provided for treating heel pain syndromes by injecting a neurotoxin into the appropriate muscle would achieve an effective result. The method can comprise administering an amount of neuromuscular toxin, such as a botulimum toxin, that is effective to treat heel pain syndromes, such as plantar fasciitis, via muscular injection to a subject in need thereof to muscles of the affected foot, such as Abductor Hallucis and Quadratus Plantae.

In some embodiments, the toxin can be any neuromuscular toxin capable of interfering with the connection between muscle and nerve. In some embodiments, the toxin is an inhibitor of acetylcholine release, such as botulinum toxin or a protein that mimics its acetylcholine release inhibiting effect. Currently, there are seven known serotypes of botulinum toxin, designated as types A through G. Other potentially useful toxins include, but are not limited to, tetanus toxins, tetrodotoxin, *difficile* toxins, *butyricum* toxins, and various animal venoms. Staphylococcal alpha-toxin can also be used, as it has also been shown to induce reversible, flaccid paralysis of skeletal muscle.

Recombinant, synthetic, and derivative neuromuscular toxins can also be used. For example, proteins produced using recombinant DNA technology which mimics the effects of these natural toxins can be used. Suitable toxins can also include proteins synthetically produced using in vitro protein synthesizing techniques well known in the art. Synthetically produced neurotoxins are also intended to include substances which have been rendered neurotoxic by a variety of manipulations, such as enzymatic or chemical processing and conjugation or derivatization with moieties which themselves are neurotoxic. Accordingly, toxins for use in connection with some embodiments include derivatives of naturally occurring toxins and other known toxins. "Derivative" means a chemical entity which is slightly different from a parent chemical entity but which still has a biological effect similar, or substantially similar, to the biological effect of the chemical entity. For example, suitable toxin derivatives can include neurotoxin components that have modified amino acid side chains, as is well known in the art.

It is also contemplated, that embodiments make use of derivatives in the form of fragments, subunits, and chimeras of neuromuscular toxins can be used. Botulinum toxin, for example, is composed of a heavy chain and a light chain, joined together by two disulfide bonds. Through disruption of the disulfide bond, the subunits can be separated and combined with other moieties, such as stabilizers or toxicity enhancers. If re-associated with other subunits or toxic substances, a biologically active chimera suitable for use in the embodiments can be produced. Toxin fragments, e.g., a portion(s) of neurotoxin that retains neurotoxic and/or biological activity, can also be used.

Neurotoxic substances that share amino acid sequence homologies and/or identities with currently known neuromuscular toxins can also be used. In addition, mixtures of toxins can also be used, where such mixtures have been selected to cause longer-lasting action than with a single toxin.

In some embodiments, the toxin may be a botulinum toxin, such as botulinum toxin type A. Commercially available from suppliers, such as Allergan (BOTOX) and Ipsen (DYSPORT), Revance Daxibotulinum toxin A (RT002), botulinum toxin type A is an artificially produced neuromuscular paralyzing agent that is currently licensed by the FDA for cervical dystonia, blepharospasm, strabismus, and wrinkles. When injected into muscle, the botulinum toxin binds to the nerve ending and blocks the nerve from releasing acetylcholine. As a result, the muscle cannot contract and effectively relaxes. Botulinum toxin type B is commercially available under the trademark MYOBLOC and has also been shown to be clinically safe and effective in treating a number of neuromuscular conditions.

The degree of muscle relaxation can be regulated by variation of dosage, variation in the method or site of administration, and frequency of administration.

The dose of toxin administered to the patient will depend upon the severity of the condition (e.g. the size of the area requiring treatment, the age and size of the patient and the potency of the toxin). One unit (U) of toxin is defined as the LD.sub.50 upon intraperitoneal injection into female Swiss Webster mice weighing 18 to 20 grams each. Typically, the dose administered to the patient may be from about 1 to about 1000 units. In one embodiment, the dosage for botulinum toxin type A may be from about 50 units to about 300 units. Although such a maximum far exceeds the dosage employed in the treatment of blepharospasms and dystonias (10-150 U), it is well below the lethal dose for humans (estimated to be about 3000 U). In some embodiments, the range of dosage of botulinum toxin type A is from about 75 units to about 100 units. In other embodiments, the range of dosage of botulinum toxin type A may be less than 75 units or greater than 100 units.

Those of ordinary skill in the art will know of or can readily determine without undue experimentation other suitable dosages for other neuromuscular toxins.

The analgesic effects of injection of botulinum toxin A and/or B may last indefinitely, or may last for about 3 to about 6 months, depending on the patient. If symptoms recur, toxin can be readministered as needed. Frequency of administration for other neuromuscular toxins can be determined using routine experimentation by those skilled in the art.

As described above, the method of administering the selected toxin is by injection into the target muscle. Intramuscular injection can be accomplished using any suitable injection device. For example, a 27-gauge needle in a 3-cc tuberculin syringe can be used to deliver the toxin directly into the muscle. Needle-less injection systems can also be used to inject the toxin into the target muscle.

Treatment is affected by injections of toxin into the insertional plantar fascia area of each of the Abductor Hallucis and Quadratus Plantae muscles in a foot of the patient affected by the Plantar Heel Pain Syndrome. Thus, toxin can be injected at the intrinsic foot muscle origins of each of the Abductor Hallucis and Quadratus Plantae muscles at the plantar medial calcaneus. The injections at each of these muscles can be conducted in either order and can occur during the same procedure or can be separated in time by one to twenty-four hours, or by one day to three weeks or as long as three months. However, in certain preferred embodiments, an injection of toxin is first made into the Abductor Hallucis and then in the same procedure into the Quadratus Plantae.

In some embodiments, proper placement of injection sites can be confirmed using a nerve/muscle stimulator. For example, a DigiStim III; Neuro Technology Inc, Kerrville, Tex., can be employed to confirm proper placement of injection sites. These can make use of a needle electrode, such as Neuro-line Inoject; Ambu, Ballerup, Denmark, which can be both stimulated to confirm proper placement by evaluation of muscle subjected to stimulation and then used for delivery of toxin.

For delivery of injections, a patient can be placed supine to allow placement of leads for muscle stimulation and placement of the needle electrode. Stimulation can be at any frequency known to stimulate muscles, such as 2-Hz. The needle can be gently advanced into the abductor muscle towards its origin. A low frequency is used to confirm the motor response of the abductor hallucis with visible contraction of the muscle and corresponding adduction of the hallux. At this point toxin can be administered. The needle can then be partially retracted and redirected toward the origin of the quadratus plantae muscle origin at the plantar medial process of the calcaneus. Care is preferably taken in obtaining the motor response from the correct muscle by avoiding stimulation of the muscles in the surrounding area by using a high frequency. The needle is gently advanced until flexion of the lesser digits at the distal inter-phalangeal joints is observed. Toxin is then administered. The dose selected can be selected based on the use of BTX A in similar studies treating plantar fasciitis. 27-31, 43-45

The techniques described herein can be used in conjunction with other techniques to further relieve pain caused by plantar fasciitis. For example, botulinum toxin can be injected directly into the plantar fasciitis to provide additional relief.

A needling technique, such as dry needling, intramuscular stimulation or myofascial trigger point needling, into the plantar fascia can also be incorporated to further ameliorate pain associated with plantar fasciitis. For example, a solid filiform needle or a hollow-core hypodermic needle can be inserted into the plantar fascia.

Botulinum toxin can also be applied topically to the skin in the area of pain caused by plantar fasciitis as proposed. Although various forms of botulinum toxin are suitable for this purpose, RT002, a form of botulinum toxin developed by Revance, in Newark, Calif., can be effective for this purpose.

In the following examples, four case reports with distinct differing presentations of Plantar Heel Pain Syndrome treated with this novel BTX A injection paradigm show the results of treating a challenging multi-etiological condition frequently diagnosed singularly as plantar fasciitis.

EXAMPLES

The following examples are non-limiting.

Example 1—Materials and Methods

Materials used were a nerve/muscle stimulator (DigiStim III; Neuro Technology Inc, Kerrville, Tex.); a lead wire with a gel electrode; a needle electrode (Neuro-line Inoject; Ambu, Ballerup, Denmark), 35×0.40 (1.4 inches×27 gauge), with a 30-cm lead wire; 100 U of BTX A solubilized in 0.9% sterile saline without preservative; and a 3-mL sterile syringe with a draw needle.

The patient was placed supine with the low-voltage lead (gel electrode) placed on the posterior lower leg. Lead wires are attached to the DigiStim jacks. The Inoject needle attached to the DigiStim was placed just distal to the plantar medial heel sulcus at the proximal abductor hallucis muscle directed posterior proximal at approximately forty-five degrees to both the transverse and sagittal planes of the foot.

The DigiStim was turned on and the 2-Hz button depressed, allowing for a frequency of two pulses per second to be introduced into the needle. The needle was gently advanced into the abductor muscle towards its origin. A low frequency was used to confirm the motor response of the abductor hallucis with visible contraction of the muscle and corresponding adduction of the hallux. At this point fifty units of toxin was administered. The needle was then partially retracted and redirected toward the origin of the quadratus plantae muscle origin at the plantar medial process of the calcaneus. Care was taken in obtaining the motor response from the correct muscle by avoiding stimulation of the muscles in the surrounding area by using a high frequency. The needle was gently advanced until flexion of the lesser digits at the distal inter-phalangeal joints was observed. Fifty units of toxin were then administered. The dose selected was based on the use of BTX A in similar studies treating plantar fasciitis. 27-31, 43-45

Example 2—Patient Inclusion Criteria

Age over 18 years with heel pain for 3 months and a baseline VAS of 4 or more for heel pain in the last 48 hours and one or more of the following:

1. US positive for thickened >4 mm PF.
2. Inability to abduct the 5$^{th}$ toe.
3. Positive Tinel's sign or Valleix's Point to one or more of the posterior tibial nerve, lateral plantar nerve, medial plantar nerve, infra-calcaneal nerve, medial calcaneal nerve.
4. Post-static dyskinesia.
5. Plantar medial heel pain with Phalen's maneuverer.
6. Plantar medial fascial heel pain with tension.

Example 3—Patient Exclusion Criteria

Patients were excluded if they had any one of the following:

Calcaneal bone cyst.
Rearfoot soft tissue masses/bursae, tendon pathology.
Plantar heel calcifications.
Rearfoot dermal conditions.
Prior treatment with BTX in the lower extremity.
History of coagulopathies.
History of rear-foot or ankle surgery.
History of HIV.
Aminoglycosides.
Myastania Gravis.
Pregnancy or lactation.
Alcoholism or drug abuse.
Narcotic pain medication.
History of systemic disorders arthritis/fibromyalgia/spondylolisthesis/radiculopathy/sciatica.
Rear foot fracture.
Heel fat pad atrophy.
Trauma.
Other conditions of ambulatory disability.

Example 4—Baseline Assessment

At the initial baseline/pre-injection visit patients were assessed clinically. Initial function was scored with the Foot and Ankle Ability Measure (FAAM) 52 and Plantar Fasciitis Pain/Disability Scale (PFPS) which includes a visual analog scale (VAS) 53. All patients were instructed to cease any prior non-operative treatments including RICE, cortisone injection, PRP, prolotherapy, PT, night splint, NSAID's. Continued use of shoe inserts or custom orthotics were permitted as well as any prior shoe modification and lower extremity stretching exercises. Patient were advised to maintain their normal daily and athletic activities as tolerated. Follow up examinations were at; 1 week, 3 weeks, 6 weeks, 12 weeks and 26 weeks post-injection with FAAM and VAS scores assessed (previous 48 hours). PFPS scores (previous 6 weeks) were done at 6, 12- and 24-weeks post-injection. (Higher VAS score=increased pain. A lower FAAM score=increased disability. A higher PFPS score=increased disability).

Example 5—Case Report (Plantar Fasciitis)

An otherwise healthy daily athletic 59-year-old male presented with a 4-month history of left plantar medial heel pain. Three months of conservative treatments which included change in shoe gear, NSAID's, stretching, icing and custom orthotics were not satisfactorily effective. Findings were positive for exquisite palpable left plantar medial fascial heel pain with tension, daily post-static dyskinesia. Negative to Phalen test. US finding of (5 mm) thickened plantar fascia distal to insertion. The rest of the podiatric exam was unremarkable including WB foot radiographs.

Unwilling to pursue other conservative treatments including cortisone injections, the patient opted for BTX A injection.

48-hour VAS and FAAM at pre-injection and 1,3,6,12 and 26 weeks post-injection and PFPS at pre-injection and 6,12- and 26-weeks post-injection.

TABLE 1

| Patient #1 | Pre-injection | 1-week P.I. | 3-week P.I. | 6-week P.I. | 12-week P.I. | 24-week P.I. |
|---|---|---|---|---|---|---|
| V.A.S./100 | 80 | 45 | 20 | 15 | 0 | 0 |
| FAAM | 50% | 85% | 91% | 97% | 100% | 100% |
| PFPS | 73.6 | | | 13.2 | 0 | 0 |

Example 6—Case Report (Plantar Fasciosis/Tarsal Tunnel Syndrome)

A 50-year-old otherwise healthy female with over 2 year progressively painful right plantar medial heel. Previous treatments included; cortisone injection, custom orthotics, physical therapy, night splint, stretching, icing and NSAID's. Findings included sub fascial pain with palpation to the plantar medial heel with positive Tinel's to both plantar medial arch and Valleix's Point to infra-calcaneal nerve (Baxter's). Positive to Phalen test. Plantar medial sensory loss. Positive US insertional thickening of the plantar fascia. Weakness to abduction $5^{th\ toe}$. The rest of the podiatric exam was unremarkable. No plantar calcaneal spur on lateral radiograph.

48-hour VAS and FAAM at pre-injection and 1,3,6,12 and 26 weeks post-injection and PFPS at pre-injection and 6,12- and 26-weeks post-injection.

TABLE 2

| Patient #1 | Pre-injection | 1-week P.I. | 3-week P.I. | 6-week P.I. | 12-week P.I. | 24-week P.I. |
|---|---|---|---|---|---|---|
| V.A.S./100 | 75 | 50 | 30 | 20 | 10 | X |
| FAAM | 33% | 70% | 89% | 91% | 92% | X |
| PFPS | 88 | | | 20.4 | 13 | X |

Example 7—Case Report (Plantar Fasciitis/Baxter's Neuritis)

A 70-year-old otherwise healthy decades avid runner with five months of daily left heel pain causing him to cease running. Minimal relief with change in shoes, custom orthotics, three cortisone injections, stretching and massage icing. Positive with Ultrasound for insertional thickening (6 mm) of the plantar fascia. Plantar medial palpable fascial pain with tension and sub fascial pain and with Valleix's Point to the infra-calcaneal nerve. Positive to Phalen test. Plantar calcaneal spur in lateral radiograph. Weakness to abduction of the left $5^{th}$ toe. The rest of the podiatric exam was unremarkable.

48-hour VAS and FAAM at pre-injection and 1,3,6,12 and 26 weeks post-injection and PFPS at pre-injection and 6,12- and 26-weeks post-injection.

TABLE 3

| Patient #1 | Pre-injection | 1-week P.I. | 3-week P.I. | 6-week P.I. | 12-week P.I. | 24-week P.I. |
|---|---|---|---|---|---|---|
| V.A.S./100 | 80 | 30 | 30 | 25 | 20 | X |
| FAAM | 56% | 64% | 92% | 95% | 73 | X |
| PFPS | 59.6 | | | 36 | 41 | X |

Example 8—Case Report (Plantar Fasciosis)

A 55-year-old otherwise healthy female with over 3-year intermittent left plantar heel pain now constant and progressive in the last 3 months throughout day and worse standing. Some relief with heat and massage. Minimal relief with conservative treatments of NSAID's, OTC and custom orthotics, various shoes, cortisone injections and physical therapy. Plantar medial heel pain with and without fascial tension left foot. Negative Phalen test. Previous HAV corrective surgery with distal osteotomy. The rest of the podiatric exam was unremarkable.

Prior 48-hour VAS and FAAM at pre-injection and 1,3, 6,12 and 26 weeks post-injection and PFPS at pre-injection and 6,12- and 26-weeks post-injection.

TABLE 4

| Patient #1 | Pre-injection | 1-week P.I. | 3-week P.I. | 6-week P.I. | 12-week P.I. | 24-week P.I. |
|---|---|---|---|---|---|---|
| V.A.S./100 | 80 | 50 | 40 | 25 | 20 | 10 |
| FAAM | 45% | 76% | 78% | 89% | 96% | 96% |
| PFPS | 75 | | | 23 | 13.4 | 10 |

Example 9—Results

The results show an improvement in pain and function across all three assessment scales; VAS, FAAM and PFPS, for all four patients with distinctly different presentations of Plantar Heel Pain Syndrome. There is a consistent significant improvement at 6 weeks post-injection which sustains up though the 24-week assessments regardless of etiology of the HPS. * (X) assessment pending December 2018. There was no muscle atrophy or loss of foot structure noted at the follow-up examinations of these four patients.

Example 10—Discussion

This novel Injection paradigm may be a valuable early intervention for Plantar Heel Pain Syndrome before considering costlier and less efficacious prolonged treatments and tests that may only address a singular etiology. Certainly, a large well controlled study will be needed to bear this out or not.

The inventor has often found Plantar Heel Pain Syndrome and its manifestations are related to a compression of the medial/plantar nerve complex of the heel between the Quadratus Plantae and/or the Abductor Hallucis muscles. Specifically, one, or a combination, of the medial plantar nerve, lateral plantar nerve, first branch of the lateral plantar nerve or variant thereof, and the dense neuro-ganglia within the Quadratus Plantae at its calcaneal origin.

Clinical/surgical experience has been that patients with recalcitrant Plantar Heel Pain Syndrome, regardless of the variable pathology who have failed conventional conservative heel pain treatments obtain resolution with surgical decompression between these intrinsic foot muscles. Therefore, without wishing to be bound by any particular theory, injecting BTX A specifically into these two muscles for temporary paralysis is believed to act as a neurological decompression in a manner similar to that achieved surgically, thereby breaking the pathological pain cycle. It is also believed that injection of toxin obtains direct neuron-analgesic and musculoskeletal anti-inflammatory benefit from the toxin's diffusion to the plantar medial heel area which could account for some success of indiscriminate injection of BTX A to the plantar medial heel area for plantar fasciitis as seen in prior studies.

Also, one must consider there are differences in diffusion of the various commercially available BTX A products and those which may have less such as Xeomin, may benefit from additional deposition of toxin to the trigger point area of pain and plantar fascia.

Example 11—Conclusion

Patients presenting with heel pain are commonly inaccurately diagnosed as having plantar fasciitis (used as a catch all) when in fact the diagnosis is a syndrome of several distinct pathologies that may or may not include plantar fasciitis. They include; tarsal tunnel syndrome, medial or lateral plantar nerve entrapment, "Baxter's Neuritis", mechanically induced intrinsic muscle inflammation, insertional calcaneal enthesopathy and plantar fasciosis. This small investigation of case reports may offer insight into a more global efficacy using a very specific injection paradigm that considers the multifactorial etiologies of Heel Pain Syndrome and botulinum toxin's local efficacy with temporary muscle paralysis, analgesic and anti-inflammatory properties.

Long term relief and prophylaxis against recurrence may likely require addressing the underlying, mechanical, inflammatory or degenerative processes of the Syndrome, or if initially effective, possibly additional BTX injection at one to two-year intervals.

Clearly a larger and higher-level placebo controlled blinded study is needed to challenge the viability of this treatment in the general population for the multifactorial Plantar Heel Pain Syndrome condition.

REFERENCES

All references herein are incorporated by reference in their entireties.
1. Buchbinder R. Clinical practice: Plantar Fasciitis. N Engl J Med 350: 2159, 2004.
2. Riddle D L, Pulisic M, Pidcoe P, Johnson R E: Risk factors for plantar fasciitis: a matched case-control study. J Bone Joint Surg 85A: 872, 2003.
3. Mardani-Kivi M, Mobarakeh M K, Hassanzadeh Z, et al: Treatment Outcomes of Corticosteroid Injection and Extracorporeal Shock Wave Therapy as Two Primary Therapeutic Methods for Acute Plantar Fasciitis: A Prospective Randomized Clinical Trial. JFAS 54: 1047, 2015.
4. Pribut S M: Current Approaches to the Management of Plantar Heel Pain Syndrome, Including the Role of Injectable Corticosteroids. JAPMA 97: 68, 2007.
5. Barrett S J: Podiatrytoday.com/article/4735.
6. Schneider H P, Baca J M, Carpenter B B, et al: American College of Foot and Ankle Surgeons Clinical Consensus Statement: Diagnosis and Treatment of Adult Acquired Infra-Calcaneal Heel Pain. JFAS 57: 370, 2018.
7. Tahririan M A, Motififard M, Tahmasebi M N, et al: Plantar Fasciitis. J Res Med Sci 17(8): 799, 2012.
8. Melero-Suarez R, Sanchez-Santos J A, Dominguez-Maldonado G: Evaluation of the Analgesic Effect of Combination Therapy on Chronic Plantar Pain through the Myofascial Trigger Points Approach. JAPMA 108: 27, 2018.
9. Hendrix C L, Jolly G P, Garbalosa J C: Entrapment Neuropathy: The Etiology of Intractable Chronic Heel Pain Syndrome. JFAS 37: 273, 1998.
10. Lemont H, Ammirati K M, Usen N: Plantar Fasciitis. A Degenerative Process (Fasiosis) Without Inflammation. JAPMA 93: 234, 2003.
11. Mahowald S, Legge B S, Grady J F: The Correlation Between Plantar Fascia Thickness and Symptoms of Plantar Fascia. JAPMA 101: 385, 2011.
12. Myerson M S: Chapter 34, Plantar Heel Pain, Foot and Ankle Disorders, Vol Two, Edited by G B Pfeffer, p 838, W B Saunders, Philadelphia, 2000.
13. Coughlin M J: Chapter 12, Plantar Heel Pain, Surgery of the Foot and Ankle, $8^{th}$ ed., Vol. 1, Edited by T H Lee, P B Maurus, p 695, Mosby 2007.
14. Ugurlar M, Sonmez M M, Ugurlar O Y, et al: Effectiveness of Four Different Treatment Modalities in the Treatment of Chronic Plantar Fasciitis During a 36-Month Follow-Up Period: A Randomized Controlled Trial. J Foot Ankle Surg, 57: 913, 2018.
15. Rahbar M, Eslamian F, Toopchizadeh V. A Comparison of the Efficacy of Dry-needling and Extracorporeal Shockwave Therapy for Plantar Fasciitis: A Randomized Clinical Trial. Iran Red Crescent Med J; 20(9), 2018.
16. Zelen C M, Poka A, Andrews J: Prospective, Randomized, Blinded, Comparative Study of Micronized, Dehydrated, Amniotic/Chorionic Membrane Allograft for Plantar Fasciitis-A Feasibility Study. Foot Ankle Int XX(X) 1-8, 2013.
17. Sammarco G J, Helfrey R B: Surgical Treatment of Recalcitrant Plantar Fasciitis. Foot Ankle Int 9: 520, 1996.
18. Cheung J T, An K N, Zhang M: Consequences of Partial and Total Plantar Fascia Release: A Finite Element Study. Foot Ankle Int: 2, 125, 2006.
19. Hambleton P, Moore A P: "Botulinum Neurotoxins: Origin, Structure, Molecular Actions and Antibodies," in Handbook of Botulinum Toxin Treatment, ed by A P Moore, p 16, Blackwell Science Ltd, Oxford, England, 1995.
20. Simpson L L: "Current Concepts on the Mechanism of Action of Clostridial Neurotoxins," in Botulinum and Tetanus Neurotoxins, ed by B R Das Gupta, p 5, Plenum Press, New York, 1993.

21. Biglan A W, Burnstine R A, Rogers G L, et al: Management of strabismus with botulinum toxin A. Ophthalmology 96: 935, 1989.
22. Suputtitada A: Local botulinum toxin type A injections in the treatment of spastic toes. Am J Phys Med Rehabil 81: 770, 2002.
23. Radovic P A, Shah E: Nonsurgical Treatment of Hallux Abducto Valgus with Botulinum Toxin A. JAPMA 98: 61, 2008.
24. Wu K P, Chen C K, Lin S C, et al: Botulinum Toxin type A injections for patients with painful hallux valgus: a double-blind, randomized controlled study. Clinical Neurology and Neurosurgery 129: S58, 1015.
25. Chen J T, Chen C K, Tang A C, et al: Effective Conservative Treatment for Managing Painful Hallux Valgus. Medical Research Archives, KEI J 4: 2, 2016.
26. Moghtaderi A, Dehghan F, Mousavizadeh A, et al: Evaluation of the Therapeutic Effect of Botulinum toxin A on Hallux Valgus Deformity and Pain. Int J Phys Med Rehabil 5: 6, 2017.
27. Ahmad J, Ahmad S H, Jones K: Treatment of Plantar Fasciitis with Botulinum Toxin: A Randomized Controlled Study. Foot Ankle Int 38: 1, 2016.
28. Babcock M S, Foster L, Pasquina P, et al: Treatment of Pain Attributed to Plantar Fasciitis with Botulinum Toxin: A Short-Term, Randomized, Placebo-Controlled, Double-Blind Study. Am. J. Phys. Med. Rehabil. 84: 649, 2005.
29. Huang Y C, Wei S H, Wang H K, et al: Ultrasonic Botulinum Type A for Plantar Fasciitis: An Outcome-Based Investigation For Treating Pain And Gait Changes. J Rehabil Med 42: 136, 2010.
30. Placzek R, Deuretzbacher G, Nat R: Treatment of chronic plantar fasciitis with Botulinum toxin A: preliminary clinical results. Clin J Pain 22: 190, 2006.
31. Placzek R, Deuretzbacher G, Buttgereit F, et al: Treatment of chronic plantar fasciitis with Botulinum toxin A: an open case series with a 1 year follow up. Annals of the Rheumatic Diseases 64: 1, 2005.
32. Borodic G E, Acquadro M, Johnson E A: Botulinum toxin therapy for inflammatory disorders: mechanisms and therapeutic effects. Expert Opinion Investig Drugs 10: 1531, 2001.
33. Mustafa G, Anderson E M, Bokrand-Donatelli Y, Neubert J K, et al: Anti-nociceptive effect of conjugate of substance P and light chain of botulinum neurotoxin type A. Pain 154: 1, 2013.
34. Singh J: Use of botulinum toxin in musculoskeletal pain. F1000Research 2:52 1-22, 2013.
35. Zhang T, Adatia A, Zarin W, et al: The efficacy of botulinum toxin type A in managing chronic musculoskeletal pain: a systemic review and meta-analysis. Inflammopharmacol 19: 21, 2011.
36. Rivera R, Arcila M, Avellaneda M, et al: Botulinum toxin treatment of chronic pain. Review of the evidence. Rev Columb Anestesiol 42: 205, 2014.
37. Cui M, Khanijou S, Rubio J, et al: Subcutaneous administration of botulinum toxin A reduces formalin-induced pain. Pain 107: 125, 2004.
38. Cheshire W P, Abashian S W, Mann J D: Botulinum toxin in the treatment of myofascial pain syndrome. Pain 59: 65, 1994.
39. Silberstein S, Mathew N, Saper J, et al: Botulinum type A as a migraine preventive treatment. For the BOTOX Migraine Clinical Research Group. Headache 40: 445, 2000.
40. Wheeler A H, Goolkasian P, Gretz S S: A randomized, double-blind, prospective pilot study of botulinum toxin injection for refractory, unilateral, cervicothoracic, paraspinal, myofascial pain syndrome. Spine 1; 23: 1662, 1998.
41. Jarvis S K, Abbott J A, Lenart M B, et al: Pilot study of botulinum toxin type A (BOTOX) injected into the levator ani muscles of women with objective pelvic floor muscles spasm decreases pain symptoms and improves quality of life. Aust N Z J Obste Gynaecol 44: 46, 2004.
42. Foster L, Clapp L, Erickson M, et al. Botulinum toxin A and chronic low back pain: a randomized, double-blind study. Neurology 22; 56: 1290, 2001.
43. Peterlien C D, Funk J F, Holscher A, et al: Is botulinum toxin A effective for the treatment of plantar fasciitis? Cin J Pain 28(6):527, 2012.
44. Diaz I V, Rodriquez C M, Mulet S, et al: Randomized controlled study of the efficacy of injection of botulinum toxin type A versus corticosteroids in chronic plantar fasciitis: Results at one and six months. Clinical Rehabilitation 26(7):594, 2011.
45. Diaz-Llopis I V, Gomez-Gallego D, Mondejar-Gomez F J, et al: Clin Rehabil; 27(8):681, 2013.
46. Coughlin M J, Surgery of the Foot and Ankle, $8^{th}$ ed., Vol. 1, 663-670, Mosby 2007.
47. Donovan A, Rosenberg Z S, Cavalcanti C F: MR Imaging of Entrapment Neuropathies of the Lower Extremity Part2. The Knee, Leg, Ankle, and Foot. RadioGraphics 30:1001, 2010.
48. DeHeer P: A Closer Look at Heel Pain and Baxter's Neuritis. Podiatry Today Aug. 14, 2013.
49. Benjamin M. The Fascia of the Limbs and Back-A Review. J Anat 214(1):1, 2009.
50. Stecco C, Corradin M, Macchi V, et al: Plantar Fascia Anatomy and its Relationship with Achilles Tendon and Paratenon. J Anat. 223: 665, 2013.
51. Maida E, Presley J C, Murthy N, et al: Sonographically Guided Deep Plantar Fascia Injections. J Ultrasound Med 32:1451, 2013.
52. Martin R L, Irrgang J J, Burnett R G, et al: Evidence of Validity for the Foot and Ankle Ability Measure (FAAM) Foot Ankle Int. 26 No. 11/November 2005.
53. Willis B, Lopez A, Perez A, et al: Pain Scale for Plantar Fasciitis. The Foot and Ankle Online Journal 2: 5, 2009.
54. Soysa A, Hiller C, Refshauge K, et al: Importance and Challenges of Measuring Intrinsic Foot Muscle Strength. J Foot Ank Res, 5:29, 2012.

What is claimed is:

1. A method of treating Plantar Heel Pain Syndrome in a patient in need thereof, said method comprising injecting a botulinum toxin into the insertional plantar fascia area of each of the Abductor Hallucis and Quadratus Plantae muscles in a foot of the patient affected by the Plantar Heel Pain Syndrome, wherein the Plantar Heel Pain Syndrome is selected from the group consisting of Baxter's neuritis, Tarsal Tunnel Syndrome Heel spur Syndrome, Plantar fasciosis resulting from symptoms of plantar fasciitis of duration longer than six months, medial plantar nerve entrapment, lateral plantar nerve entrapment, medial calcaneal nerve entrapment, mechanically induced intrinsic muscle inflammation, and insertional calcaneal enthesopathy.

2. The method of claim 1, wherein the botulinum toxin is injected using a needle.

3. The method of claim 1, wherein the botulinum toxin is injected into both the Abductor Hallucis and Quadratus Plantae in the same procedure.

4. A method of treating Plantar Heel Pain Syndrome/Plantar Fasciitis in a patient in need thereof, said method comprising injecting botulinum toxin into the insertional plantar fascia area of each of the Abductor Hallucis and Quadratus Plantae muscles in a foot of the patient affected by the Plantar Heel Pain Syndrome, wherein toxin is first injected into the Abductor Hallucis and wherein the botulinum toxin is injected into the Quadratus Plantae more than one hour after the botulinum toxin is injected into the Abductor Hallucis.

5. The method of claim 1, further comprising injecting the botulinum toxin into plantar fascia in the foot of the patient.

6. The method of claim 1, wherein the botulinum toxin is administered under electronic stimulation.

7. The method of claim 1, wherein the botulinum toxin is injected only into the Abductor Hallucis and Quadratus Plantae muscles in the foot of the patient affected by the Plantar Heel Pain Syndrome.

8. The method of claim 1, wherein the heel pain syndrome is selected from the group consisting of Tarsal Tunnel Syndrome, Baxter's Neuritis, and Plantar Fasciosis.

9. The method of claim 1, wherein the placement of the needle at the insertional plantar fascial area of each of the Abductor Hallucis and Quadratus Plantae muscles is confirmed by muscle/nerve stimulation.

10. The method of claim 1, wherein the heel pain syndrome is selected from the group consisting of Baxter's neuritis, Tarsal Tunnel Syndrome, medial plantar nerve entrapment, lateral plantar nerve entrapment, and medial calcaneal nerve entrapment.

* * * * *